US009222126B2

(12) United States Patent
Bearinger et al.

(10) Patent No.: US 9,222,126 B2
(45) Date of Patent: Dec. 29, 2015

(54) METHODS FOR POINT-OF-CARE DETECTION OF NUCLEIC ACID IN A SAMPLE

(75) Inventors: Jane P. Bearinger, Livermore, CA (US); Lawrence C. Dugan, Modesto, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 358 days.

(21) Appl. No.: 13/115,878

(22) Filed: May 25, 2011

(65) Prior Publication Data

US 2011/0294112 A1 Dec. 1, 2011

Related U.S. Application Data

(60) Provisional application No. 61/348,169, filed on May 25, 2010, provisional application No. 61/348,155, filed on May 25, 2010, provisional application No. 61/348,160, filed on May 25, 2010.

(51) Int. Cl.

| | |
|---|---|
| ***C12P 19/34*** | (2006.01) |
| ***C12Q 1/68*** | (2006.01) |
| ***C12Q 1/70*** | (2006.01) |
| ***B01L 7/00*** | (2006.01) |
| *C07H 21/02* | (2006.01) |
| *C07H 21/04* | (2006.01) |
| *B01L 3/00* | (2006.01) |

(52) U.S. Cl.

CPC ............. *C12Q 1/6844* (2013.01); *B01L 3/5029* (2013.01); *B01L 7/52* (2013.01); *C12Q 1/689* (2013.01); *C12Q 1/701* (2013.01); *B01L 3/502776* (2013.01); *B01L 2300/0609* (2013.01); *B01L 2300/0851* (2013.01); *B01L 2300/1877* (2013.01)

(58) Field of Classification Search

CPC ........... C12Q 1/6844; C12Q 2537/101; C12Q 1/689; C12Q 1/701; B01L 2300/0609; B01L 2300/0851; B01L 2300/1877; B01L 3/502776; B01L 3/5029; B01L 7/52

See application file for complete search history.

(56) References Cited

U.S. PATENT DOCUMENTS

| | | | | |
|---|---|---|---|---|
| 5,879,635 | A | 3/1999 | Nason | |
| 5,919,622 | A | 7/1999 | Macho et al. | |
| 7,569,382 | B2 | 8/2009 | Li | |
| 7,776,011 | B2 | 8/2010 | Tennican et al. | |
| 2005/0013732 | A1* | 1/2005 | Battrell et al. | 422/58 |
| 2006/0263811 | A1* | 11/2006 | Jeon et al. | 435/6 |
| 2009/0061450 | A1* | 3/2009 | Hunter | 435/6 |
| 2009/0186357 | A1* | 7/2009 | Mauk et al. | 435/6 |
| 2011/0294112 | A1 | 12/2011 | Bearinger | |

OTHER PUBLICATIONS

Spargo, C.A. et al., Mol. Cell. Probes, vol. 10, pp. 247-256 (1996).*
Zanoli, L.M. et al., Biosensors, vol. 3, pp. 18-43 (2013).*

(Continued)

*Primary Examiner* — Teresa E Strzelecka
(74) *Attorney, Agent, or Firm* — Steinfl & Bruno, LLP

(57) ABSTRACT

Provided herein are methods and apparatus for detecting a target nucleic acid in a sample and related methods and apparatus for diagnosing a condition in an individual. The condition is associated with presence of nucleic acid produced by certain pathogens in the individual.

33 Claims, 15 Drawing Sheets

(56) References Cited

OTHER PUBLICATIONS

McClure et al. BMC Res. Notes, "*Assessment of DNA extracted from FTA cards for use on the Illumina iSelect BeadChip*" 2009, vol. 2, pp. 107-110.
Beckett et al., Am. J. Epidemiol., "*Buccal swabs and treated cards: Methodological considerations formolecular epidemiologic studies examining pediatric populations*" 2008, vol. 167, pp. 1260-1267.
Reid et al., J. Vet. Diagn. Invest., "*Performance of real-time RT-PCR for the detection of foot-and-mouth disease virus during field outbreaks in the United Kingdom in 2007*", 2009, vol. 21, pp. 321-330.
Goto et al., Biotechniques, "*Colorimetric detection of loop-mediated isothermal amplification reaction by using hydroxynaphthol blue*", 2009, vol. 46, pp. 167-172.
Notomi. et al., Nucleic Acids Research, "Loop-mediated isothermal amplification of DNA", 2000, vol. 28, e63.
Vincent et al. EMBO reports, "*Helicase-dependent isothermal DNA amplification*", 2004, vol. 5, pp. 795-800.
Mary Hoff, PLoS Biology, "*DNA Amplification and Detection Made Simple* (*Relatively*)" 2006, vol. 2, e222.
Dukes et al., Arch. Virol., "*Novel reverse transcription loop-ediated isothermal amplification for rapid detection of foot-and mouth disease virus*" 2006, vol. 151, pp. 1093-1106.
Ferris et al., Vet. Rec., "*Comparisons of original laboratory results and retrospective analysis by real-time reverse transcriptase-PCR of virological samples collected from confirmed cases of foot-and-mouth disease in the UK in 2001*", 2006, vol. 159, pp. 373-378.
PCT International Search Report mailed on Feb. 9, 2012 for PCT Application No. PCT/US2011/037983 filed on May 25, 2011 in the name of Lawrence Livermore National Security, LLC et al.
PCT Written Opinion mailed on Feb. 9, 2012 for PCT Application No. PCT/US2011/037983 filed on May 25, 2011 in the name of Lawrence Livermore National Security, LLC et al.
Bearinger, J., et al., Development and Initial Results of a Low Cost, Disposable, Point-of-Care Testing Device for Pathogen Detection, IEEE Transaction on Biomedical Engineering 2011, 58: 805-808.
Jangam, S., et al., Rapid, Point-of-Care Extraction of Human Immunodeficiency Virus Type 1 Proviral DNA from Whole Blood for Detection by Real-Time PCR, J. Clinical Microbiol. 2009, 47: 2363-2368.
Lee, S., et al., A polymer lab-on-a-chip for reverse transcription (RT)-PCR based point-of-care clinical diagnostics, Lab on a Chip 2008, 8: 2121-2127.
Lui, C., et al., Nucleic Acid-based Detection of Bacterial Pathogens Using Integrated Microfluidic Platform Systems, Sensors 2009, 9: 3713-3744.
Menassa, N., et al., Rapid Detection of Fungal Keratitis with DNA-Stabilizing FTA Filter Paper, Ivest. Opthal. 2010, 51: 1905-1910.
Restriction Requirement mailed on Oct. 9, 2013 for U.S. Appl. No. 13/115,877, filed May 25, 2011 in the name of Jane P. Bearinger et al.
European Search Opinion issued for European Patent Application No. 11787366.1 filed on May 25, 2011 in the name of Lawrence Livermore National Security, LLC mailed on Jan. 18, 2014.
European Search Report issued for European Patent Application No. 11787366.1 filed on May 25, 2011 in the name of Lawrence Livermore National Security, LLC mailed on Jan. 18, 2014.
Automated Miniturised Molecular Diagnostic System for Nucleic Acids Analysis from Sputum, retrieved from http://www.imm-mainz.de/fileadmin/upload/datein/IMM_PD_QLAB.280909-.pdf on Dec. 18, 2013.
Hatano et al., LAMP Using a Disposable Pocket Warmer for Anthrax Detection, a Highly Mobile and Reliable Method for Anti-Bioterrorism, Jpn. J. Infect. Dis. 2010, 63: 36-40.
Sauer-Budge et al., Low cost and manufacturable complete microTAS for detecting bacteria, Lab on a Chip 2009, 9: 2803-2810.
Weigl et al., Towards non-and minimally instrumented, microfluidics-based diagnostic devices, Critical Review Lab on a Chip 2008, 8: 1999-2014.
Non-Final Office Action mailed Mar. 14, 2014 for U.S. Appl. No. 13/115,877, filed May 25, 2011 in the name of Jane P. Bearinger et al.
Techne Manual for TC-142, pp. 1-52, Bibby Scientific, Issue 3, Sep. 2008.
Non-Final Office Action mailed on Apr. 14, 2015 for U.S. Appl. No. 13/115,877, filed May 25, 2011 in the name of Lawrence Livermore National Security, LLC.

* cited by examiner 4B.1    Sealing a sample from the individual within a containment vessel 4B.2    Transferring the sample to a nucleic acid binding element positioned in the containment vessel 4B.3    Purifying nucleic acid from the sample in the containment vessel 4B.4    Amplifying the target nucleic acid in the containment vessel 4B.5    Detecting amplification of the target nucleic acid in the containment vessel 4B.6    Diagnosing the condition

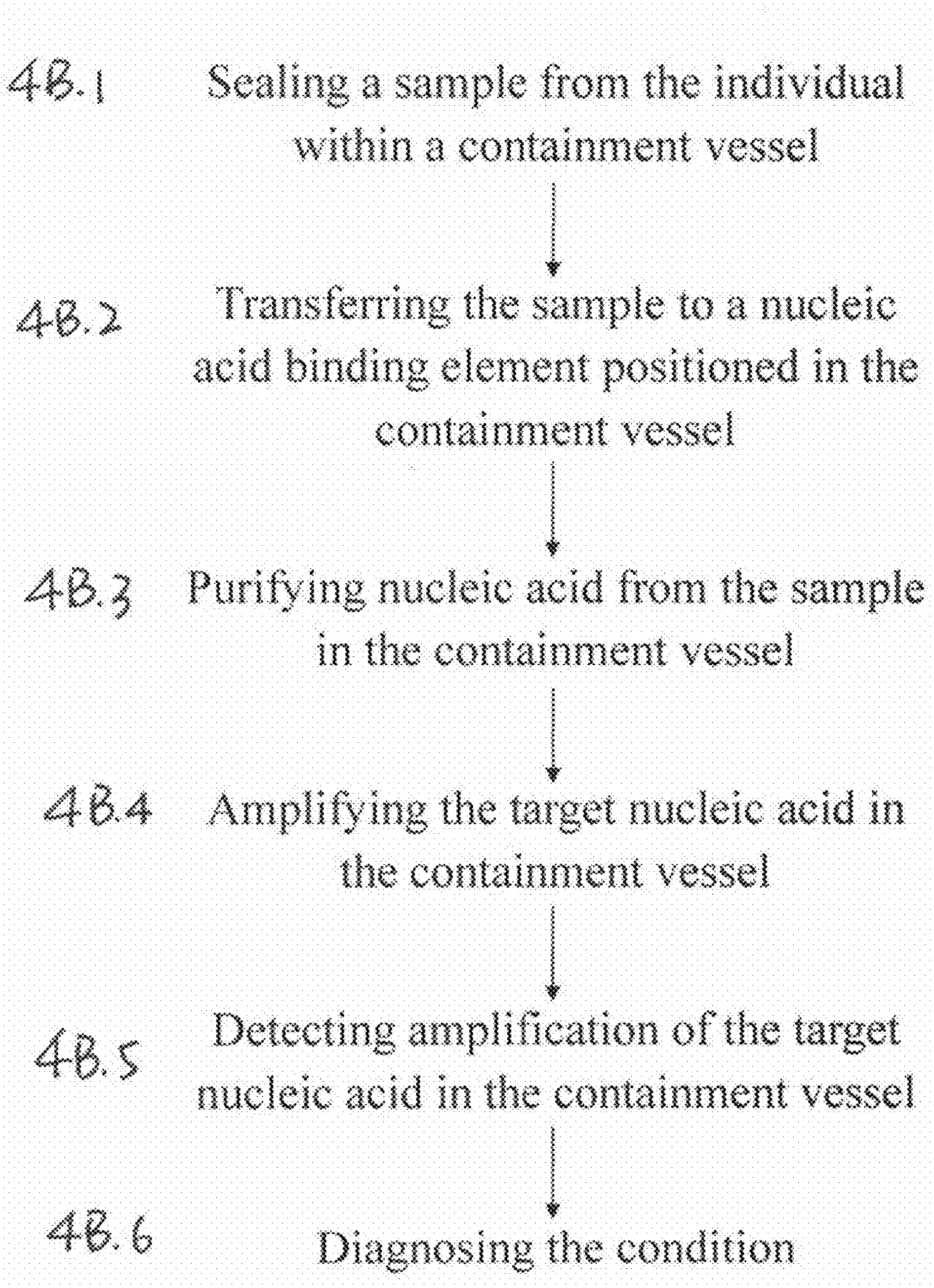

FIG. 4B 4C.1     Remove cap with hollow swab from tube 4C.2     Apply sample to swab 4C.3     Return swab to tube and snap cap closed 4C.4     Affix syringe with wash onto luer lock 4C.5     Dispense 2 ml wash and swirl 4C.6     Pipet out wash through septum    2x 4C.7     Dispense 2 ml buffer and swirl 4C.8     Pipet out wash through septum    2x 4C.9     Add Master Mix + Enzymes through septum 4C.10     Place on heating rack 4C.11     Readout assay at desired time(s)

METHODS FOR POINT-OF-CARE DETECTION OF NUCLEIC ACID IN A SAMPLE

CROSS REFERENCE TO RELATED APPLICATIONS

This application is related and claims priority to U.S. Provisional Application entitled "Disposable Sample Preparation Cartridge" Ser. No. 61/348,169, filed on May 25, 2010, U.S. Provisional Application entitled "Polymeric Method for Solution Sequestration and Release" Ser. No. 61/348,155, filed on May 25, 2010, and to U.S. Provisional Application entitled "Disposable, Inexpensive Heater for Point of Care Diagnostics" Ser. No. 61/348,160, filed on May 25, 2010, IL-12211, the disclosure of each of which is incorporated herein by reference in its entirety. The present application is also related to U.S. Patent Application entitled "Apparatus for Point-Of-Care Detection Of Nucleic Acid In A Sample" Ser. No. "13/115,877", filed on May 25, 2011, herein incorporated by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

TECHNICAL FIELD

The present disclosure relates to methods and apparatus for detecting a target nucleic acid in a sample such as a biological sample or an environmental sample, and related methods and apparatus of point-of-care detection and diagnosis of a pathogen or condition in a subject.

BACKGROUND

Early detection of epidemic outbreaks impacting public health and/or veterinary medicine needs cost-effective, robust and specific assays. Due to these needs, such assays traditionally have been conducted in centralized laboratories, rather than at the point-of-care.

However, Point-Of-Care Testing promises to bring the test to the test subject, in either the field or the clinic, providing more rapid detection with potential benefit to both the test subject and to public health.

In order to facilitate Point-Of-Care Testing, assays should be run without access to large, fragile or expensive equipment commonly found in centralized laboratories. Such equipment may include centrifuges, vortexers, thermocyclers, microscopes and incubators. Furthermore, external power sources may be unavailable in the field, and specialized technicians may not be available to conduct assays. Indeed, in some circumstances it may be desirable for test subjects to conduct self-testing.

A few companies have successfully designed high specificity Point-Of-Care Testing equipment relevant to the detection of epidemic outbreaks. To achieve high specificity, this equipment typically relies on Polymerase Chain Reaction (PCR), conducted in the field, to confirm the presence of a suspected pathogen or agent. The Bioseeq device from Smiths (Herts, U.K.) is one such hand-held instrument that can accurately detect bacterial and viral agents. Idaho's Razor (Salt Lake City, Utah) and Selex's Nexsense B (Edinburgh, U.K.) are two other commercially available systems.

Although PCR systems provide excellent specificity, they also greatly increase costs as compared to other less specific assay kits, such as an Enzyme-Linked Immunosorbent Assay (ELISA). Furthermore, PCR systems need very clean samples, necessitating large upfront investment in sample preparation platforms that effectively integrate with microfluidic sample handling and readout. As an example of PCR-based Point-Of-Care Testing capital expenditures, the Bioseeq device has a base unit price in excess of $10,000 (the base unit is used in conjunction with consumable sample insert cartridges).

In order to provide high specificity Point-Of-Care Testing equipment without necessitating formidable upfront investment by the end user, radical simplification of the processes used by current PCR-based Point-Of-Care Testing equipment is needed. Specifically, there is a need for affordable, rapid, specific and accurate Point-Of-Care Testing assays that are completely disposable, or that need only nominal upfront investment. In order to accomplish this, complex interactions at the interface of biology, chemistry and material science should be harnessed synergistically (FIG. 1).

SUMMARY

Provided herein are methods and apparatus for detecting a target nucleic acid in a sample, and related methods and apparatus for diagnosing a condition in an individual. In particular, the methods and apparatus herein described allow in several embodiments integrated sample acquisition, nucleic acid extraction, amplification and detection all in one tube, which allow rapid, point-of-care detection of nucleic acid and/or diagnosis of a condition that is associated with presence of a particular nucleic acid in an individual.

According to a first aspect of the current disclosure, apparatus for detecting a target nucleic acid in a sample is described. The apparatus comprises a containment vessel, a sample collection element configured for removable coupling to the containment vessel, a nucleic acid binding element positioned within the containment vessel. The sample collection element is configured to collect the sample and to transfer the sample to the nucleic acid binding element when the sample collection element is removably coupled to the containment vessel. The apparatus further comprises a plurality of reagents configured for placement in fluid communication with the nucleic acid binding element. The plurality of reagents comprises nucleic acid purification reagents and nucleic acid amplification reagents. The apparatus further comprises a heater configured to heat the nucleic acid amplification reagents in fluid communication with the nuclei acid binding element.

According to a second aspect of the current disclosure, apparatus for diagnosing a condition in an individual is described. The condition is associated to presence of a target nucleic acid in the individual, which is produced by certain pathogens. The apparatus comprises a containment vessel, a sample collection element configured for removable coupling to the containment vessel and optionally comprising a lumen, a nucleic acid binding element positioned within the containment vessel, a waste collection unit, a plurality of reagents, which may be enveloped within a plurality of reagent cartridges that are connected to the containment vessel, and a heater configured to heat the nucleic acid amplification reagents when the nucleic acid amplification reagents are in fluid communication with the nucleic acid binding element.

According to a third aspect of the current disclosure, methods for detecting a target nucleic acid in a sample are described. The method comprises sealing the sample within a containment vessel, transferring the sample to a nucleic acid binding element position in the containment vessel, amplifying the target nucleic acid in the containment vessel, and detecting amplification of the target nucleic acid in the containment vessel.

According to a fourth aspect of the current disclosure, a method for diagnosing a condition in an individual is described. The condition is associated to presence of a target nucleic acid in the individual, which is produced by certain pathogens. The method comprises sealing a sample from the individual within a containment vessel, transferring the sample to a nucleic acid binding element position in the containment vessel, purifying nucleic acid from the sample in the containment vessel, amplifying the target nucleic acid in the containment vessel, detecting amplification of the target nucleic acid in the containment vessel, and diagnosing the condition.

The methods and apparatus herein described allow in some embodiments inexpensive, rapid detection of a pathogen present in a sample, such as a biological sample collected from a subject or an environmental sample collected from a surface, soil, water or air and also inexpensive, point-of-care diagnosis of a condition in an individual, such as mammals and in particular human beings.

The methods and apparatus herein described can be used in connection with applications wherein detection of a pathogen is desired, including but not limited to medical application, biological analysis and diagnostics including but not limited to clinical applications.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

FIG. 4B shows a procedural flow chart of a method for diagnosing a condition in an individual.

DETAILED DESCRIPTION

Figure 1:
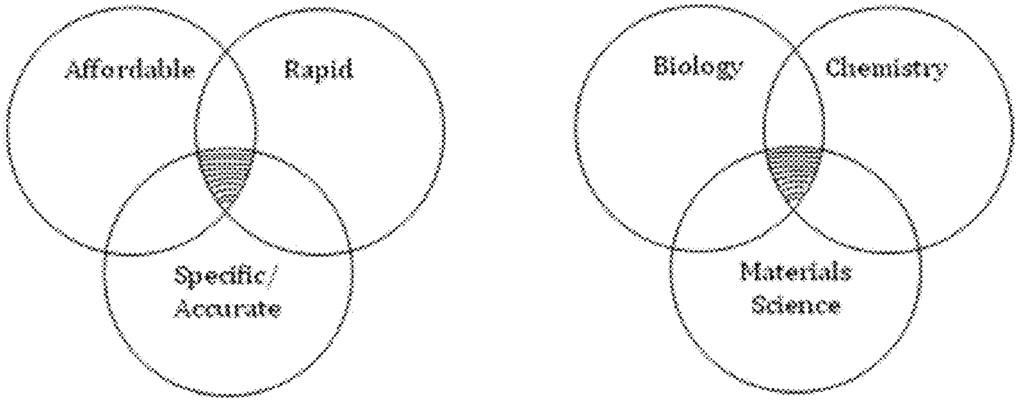
FIG. 1 shows Venn Diagrams indicating designated sweet spots of disposable point-of-care diagnostics.

Provided herein are methods and apparatus for detecting a target nucleic acid in a sample, and related methods and apparatus for diagnosing a condition in an individual. In particular, the methods and apparatus herein described allow in several embodiments integrated sample acquisition, nucleic acid extraction, amplification and detection all in one tube, which allow rapid, point-of care detection of nucleic acid and/or diagnosis of a condition that is associated with presence of a particular nucleic acid in an individual.

According to a first aspect of the disclosure, apparatus for detecting a target nucleic acid in a sample is described.

The term "apparatus" as used herein indicates a device, a machine, an instrument or a system that performs certain function according to the current disclosure.

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

The term "target" as used herein indicates an analyte of interest. The term "analyte" refers to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, amino acids, peptides proteins, nucleic acids, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state. The term "biological environment" refers to any biological setting, including, for example, ecosystems, orders, families, genera, species, subspecies, organisms, tissues, cells, viruses, organelles, cellular substructures, prions, and samples of biological origin. Exemplary targets comprise molecular targets such as small molecules, proteins, nucleic acids, and also cells, tissues and organisms.

The term "nucleic acid" as used herein indicates a polymeric form of nucleotides of any length, either ribonucleotides or deoxyribonucleotides, that comprise purine and pyrimidine bases, or other natural, chemically or biochemically modified, non-natural, or derivatized nucleotide bases. Nucleic acids of the embodiments of the current disclosure include Deoxyribonucleic acid (DNA), ribonucleic acid (RNA), or DNA copies of RNA (complementary DNA or cDNA), which may be isolated from natural sources, recombinantly produced, or artificially synthesized. The nucleic acids may exist as single-stranded or double-stranded and any chemical modifications thereof, provided only that the modification does not interfere with amplification of selected nucleic acids. For example, the backbone of the nucleic acid can comprise sugars and phosphate groups or modified or substituted sugar or phosphate groups, and a nucleic acid may comprise modified nucleotides, such as methylated nucleotides and nucleotide analogs.

In several embodiments, the methods and apparatus herein described allow isothermal amplification of a target nucleic acid in a sample. For example, in some embodiments, the isothermal amplification of a target nucleic acid is performed by the Loop-mediated Isothermal Amplification (LAMP). In some embodiments, the isothermal amplification of a target nucleic acid is performed by Helicase-Dependent isothermal Amplification (HDA). In other embodiments, the isothermal amplification of a target nucleic acid is performed by Recombinase Polymerase Amplification (RPA).

The term "isothermal amplification" as used herein indicates a method of DNA amplification using polymerase chain reaction that uses a single temperature incubation thereby obviating the need for a thermal cycler. By combining with a reverse transcription step, these amplification methods can also be used to isothermally amplify RNA.

The term "Loop-mediated Isothermal Amplification (LAMP)" as used herein indicates a isothermal nucleic acid amplification method. In LAMP, the target sequence is amplified at a constant temperature of 65° C. using either two or three sets of primers and a polymerase with high strand displacement activity. More detailed information regarding LAMP can be found in Notomi T. et al., 2000, Nucleic Acid Research, Vol. 28, e63, herein incorporated by reference in its entirety.

The term "Helicase-Dependent isothermal Amplification (HDA)" as used herein indicates another method of isothermal nucleic acid amplification wherein the use of a DNA helicase and single stranded DNA-binding proteins eliminates the need for a thermal cycler. In HDA, strands of double stranded DNA are first separated by a DNA helicase and coated by single stranded DNA-binding proteins. Two newly synthesized DNA products are then used as substrates by the DNA helicase, entering the next round of the reaction. Thus, a simultaneous chain reaction develops, resulting in exponential amplification of the selected target sequence. More detailed information regarding HDA can be found in Vincent et al., 2004, EMBO reports, Vol. 5, pp. 795-800, herein incorporated by reference in its entirety.

The term "Recombinase Polymerase Amplification (RPA)" as used herein indicates another isothermal nucleic acid amplification method wherein the use of a primer-recombinase complex and single-stranded DNA binding proteins eliminates the need for a thermal cycler. In RPA, the primer-recombinase complex attaches to the DNA template to be amplified and initiates the amplification process. Single-stranded DNA binding proteins attach to and stabilize the displaced strands of the template DNA during primer elongation by the polymerase. Two newly synthesized DNA produces are then used as substrates of the primer-recombinase complex, entering the next round of the reaction. Thus, a simultaneous chain reaction develops, resulting in exponential amplification of the selected target sequence. More detailed information regarding RPA can be found in Hoff, 2006, PLoS Biology, Vol. 2, e222 herein incorporated by reference in its entirety.

Figure 3A:
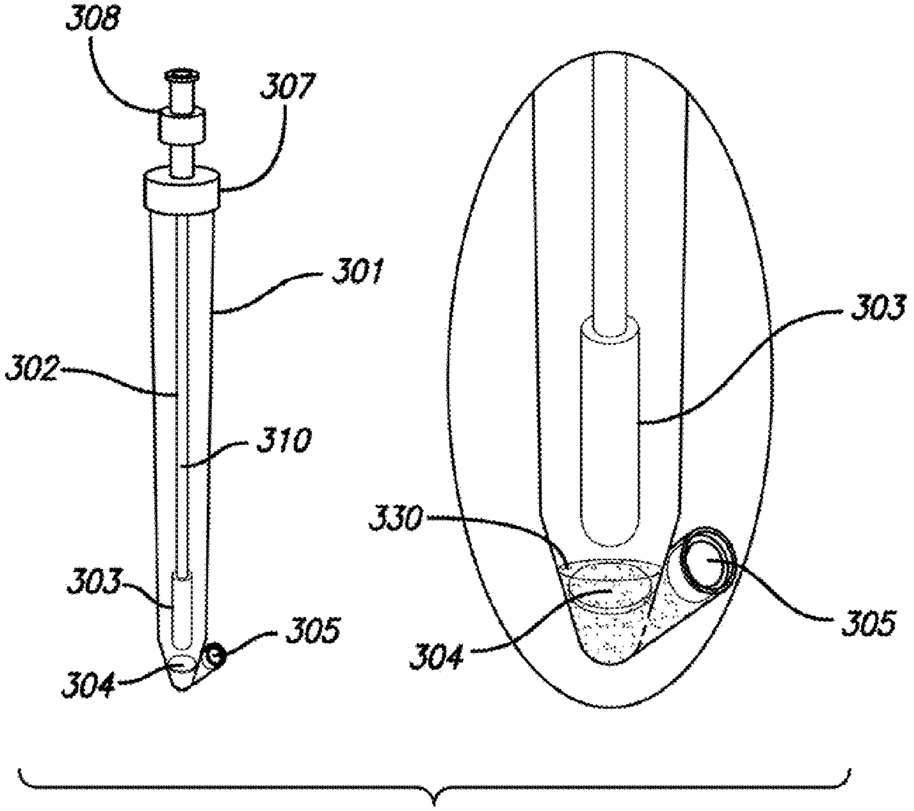
FIG. 3A shows a schematic rendering of a disposable device according to several embodiments of a first structure.

FIG. 3A shows a schematic rendering of a disposable device according to several embodiments of a first structure. The device comprises a containment vessel (301), such as a sealable polypropylene tube, a sample collection element (302), such as a hollow polyester stick, comprising a lumen (310) and a swab tip (303), a nucleic acid binding element (304), such as a 4 mm disc of cellulose FTA card, positioned within the containment vessel, and a plurality of reagents (330) comprising reagents suitable for sample preparation such as nucleic acid purification and reagents suitable for nucleic acid amplification and detection. The sample collection element is configured for removable coupling to the containment vessel.

Figure 3B:
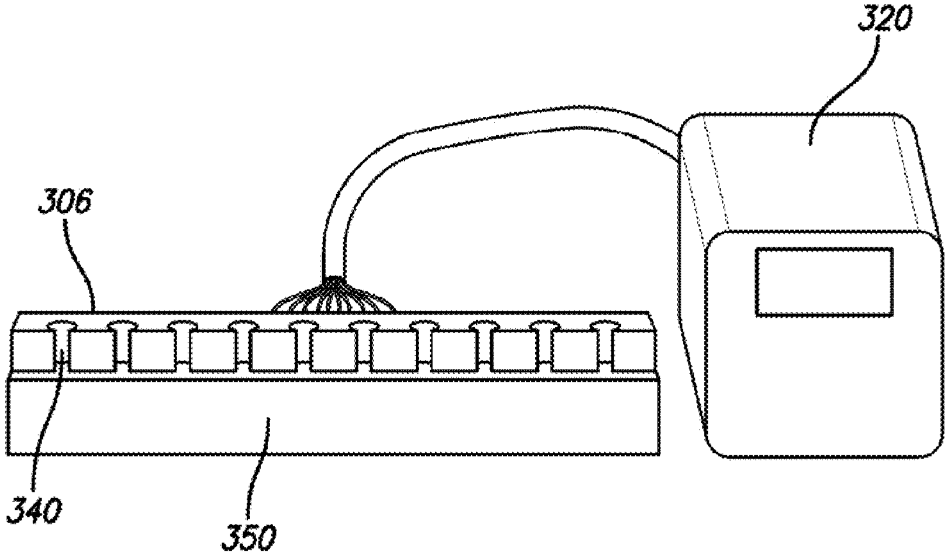
FIG. 3B shows a photograph of an electronic heater according to several embodiments.

FIG. 3B shows a schematic rendering of an electronic heater (306). The heater comprises a control unit (320) and a heating unit (350) comprising a plurality of heating blocks (340) configured to house the containment vessel (301) as in FIG. 3A, and heat the nucleic acid binding element (304).

Figure 5A:
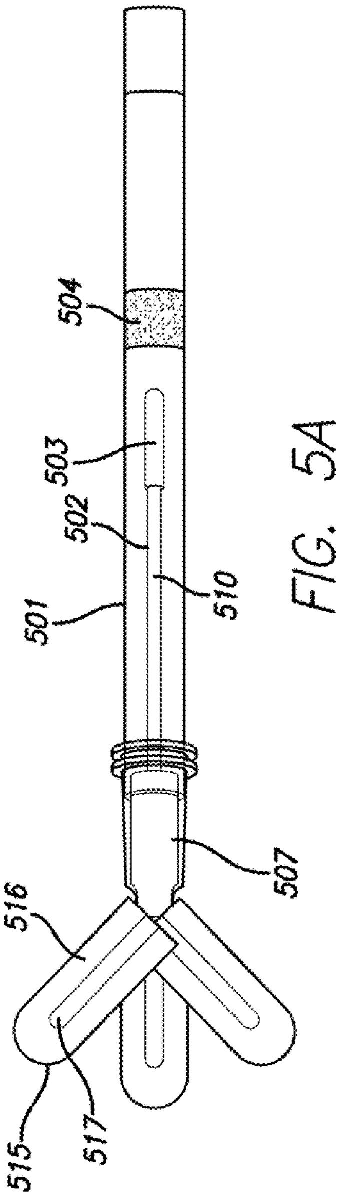
FIG. 5A shows a schematic rendering of a disposable device according to several embodiments of a second structure.

FIG. 5A shows a schematic rendering of a disposable device according to several embodiments of a second structure. The device comprises a containment vessel (501), such as a sealable polypropylene tube (501), a sample collection element (502) such as a hollow polyester stick, comprising a lumen (510) and a swab tip (503), a nucleic acid binding element (504) positioned within the containment vessel, a waste collection unit (507) coupled to the sample collection element, a plurality of reagent cartridges (515) coupled to the sample collection element and enveloping a plurality of reagents (530). The sample collection element is configured for removable coupling to the containment vessel. The plurality of reagent cartridges each comprises a capsule (516) and a plug (517). The plurality of reagents comprise reagents suitable for sample preparation such as nucleic acid purification and reagents suitable for nucleic acid amplification and detection.

Figure 5B:
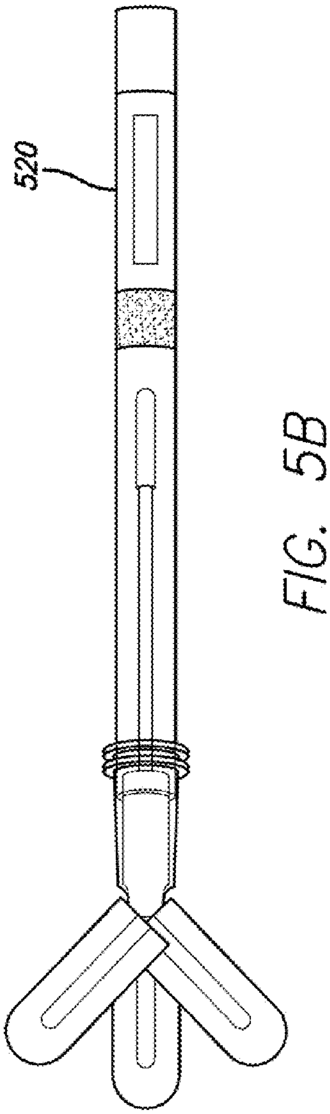
FIG. 5B shows a schematic rendering of a disposable device according to several embodiments of a third structure.

FIG. 5B shows a schematic rendering of disposable devices according to several embodiments of a third structure. The device comprises a containment vessel (501), such as a sealable polypropylene tube (501), a sample collection element (502) such as a hollow polyester stick, comprising a lumen (510) and a swab tip (503), a nucleic acid binding element (504) positioned within the containment vessel, a waste collection unit (507) coupled to the sample collection element, a plurality of reagent cartridges (515) coupled to the sample collection element and enveloping a plurality of reagents (530). The sample collection element is configured for removable coupling to the containment vessel. The plurality of reagent cartridges each comprises a capsule (516) and a plug (517). The plurality of reagents comprise reagents suitable for sample preparation such as nucleic acid purification and reagents suitable for nucleic acid amplification. The device further comprises an amplification detection unit (520) such as a Lateral Flow Dipstick (LFD).

Figure 5C:
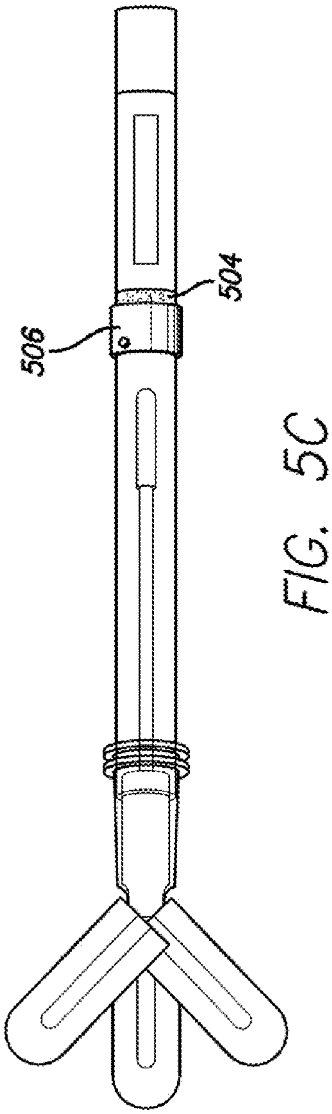
FIG. 5C shows a schematic rendering of a disposable device according to several embodiments a fourth structure.

FIG. 5C shows a schematic rendering of disposable devices according to several embodiments of a fourth structure. The device comprises a containment vessel (501), such as a sealable polypropylene tube (501), a sample collection element (502) such as a hollow polyester stick, comprising a lumen (510) and a swab tip (503), a nucleic acid binding element (504) positioned within the containment vessel, a waste collection unit (507) coupled to the sample collection element, a plurality of reagent cartridges (515) coupled to the sample collection element and enveloping a plurality of reagents (530). The sample collection element is configured for removable coupling to the containment vessel. The plurality of reagent cartridges each comprises a capsule (516) and a plug (517). The plurality of reagents comprise reagents suitable for sample preparation such as nucleic acid purification and reagents suitable for nucleic acid amplification. The device further comprises an amplification detection unit (520) such as a Lateral Flow Dipstick (LFD) and a disposable heater (506), such as a chemical heater, configured to heat the nucleic acid binding element.

Figure 6A:
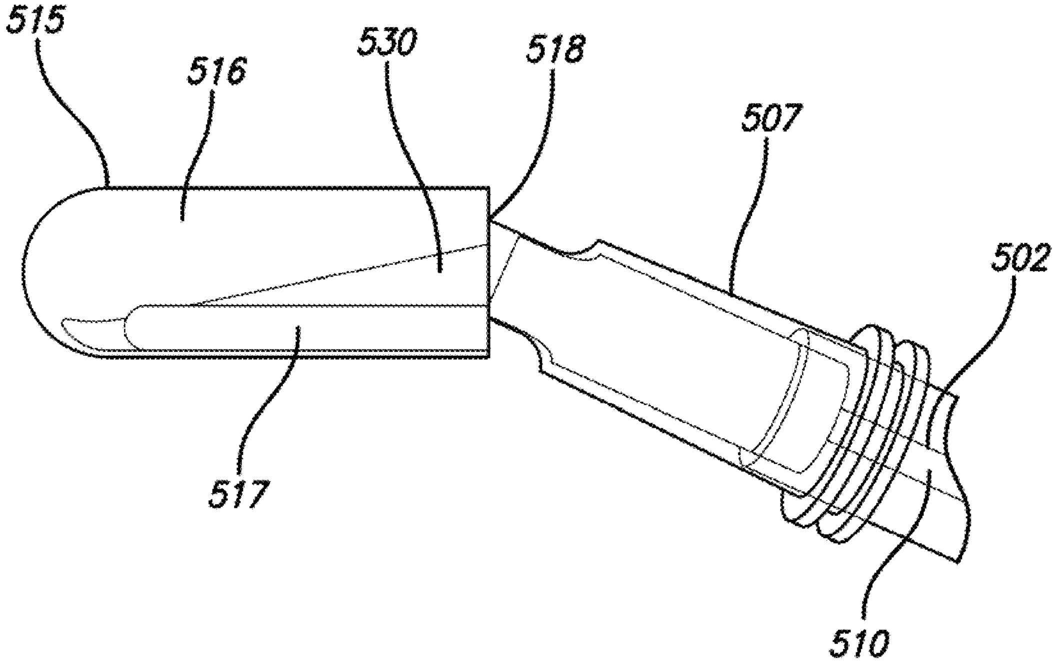
FIG. 6A shows a reagent a cartridge according to several embodiments.

FIG. 6A shows a schematic rendering of one of the plurality of reagent cartridges (515) coupled to the sample collection element (502) as shown in FIG. 5A-5B. The reagent cartridge comprises a capsule (516) and a plug (517), the capsule being connected to the lumen (510) of the sample collection element through an opening (518), the plug sealing the opening. The capsule envelopes one of the plurality of reagents (530). The reagent cartridge is configured to load the enveloped reagent through the lumen for placement in fluid communication with the nucleic acid binding element (504) upon removal of the plug from the opening.

Figure 6B:
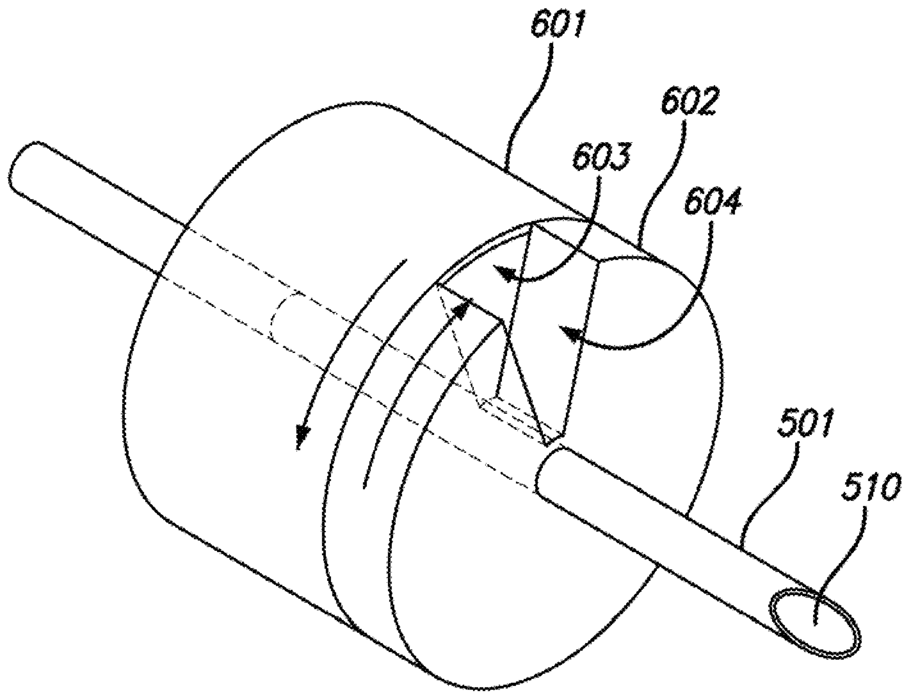
FIG. 6B shows a waste collection unit according to several embodiments.

FIG. 6B shows a schematic rendering of the waste collection unit (507) coupled to the sample collection element (502) as shown in FIG. 5A-5B. The waste collection unit comprises a chamber (601), the chamber comprising a first gap (603), and a plate (602), the plate coupled with the chamber and comprising a second gap (604). The chamber and the plate surround the lumen of the sample collection element, and at least one of the chamber and the plate is configured to be rotatable. When the first gap overlaps with the second gap, content of containment vessel (501) is adapted to flow into the waste collection unit.

According to the first aspect of the disclosure, apparatus for detecting a target nucleic acid in a sample is described. The apparatus comprises a containment vessel (301, 501), a sample collection element (302, 502) configured for removable coupling to the containment vessel, a nucleic acid binding element (304, 504) positioned within the containment vessel. The sample collection element is configured to collect the sample and to transfer the sample to the nucleic acid binding element when the sample collection element is removably coupled to the containment vessel. The apparatus further comprises a plurality of reagents (330, 530) configured for placement in fluid communication with the nucleic acid binding element. The plurality of reagents comprises nucleic acid purification reagents and nucleic acid amplification reagents. The apparatus further comprises a heater (306, 506) configured to heat the nucleic acid amplification reagents in fluid communication with the nucleic acid binding element (see FIGS. 3A-3B).

The term "reagent" as used herein indicates a substance, a compound or a mixture that is added to a system in order to bring about a chemical reaction, to see if a reaction occurs or to purify an entity from a mixture. The term "nucleic acid purification reagent" as used herein indicates a reagent that is suitable for rinsing, washing, and/or purifying nucleic acid from a mixture of entities, including but not limited to a bodily sample, an environmental sample, blood, cells, bacteria, virus and fungi. Exemplary nucleic acid purification reagents include buffer, whatman purification reagent, TE buffer, saline, lavage, and the like. The term "nucleic acid amplification reagent" as used herein indicates a reagent that is suitable for amplifying one or more target nucleic acid. The term "amplifying" as used herein indicates any process or combination of process steps that increase the amount or number of copies of a molecule or class of molecules. Nucleic acid amplification may be carried out by any reaction or combination of reactions known in the art that are appropriate as recognized by those skilled in the art. For example, amplifying a target DNA molecule may be carried out by the polymerase chain reaction (PCR), amplifying a target RNA molecule may be carried out by a sequence of making cDNA copies of the target RNA, using PCR to increase the copy number of cDNA, and transcribing the cDNA copies to obtain RNA molecules having the same sequence as the target RNA molecule. Exemplary nucleic acid amplification reagents include polymerase such as BST polymerase, dNTPs, MgSO4, betaine, suitable buffers. Selection of the reagents to be used in the methods or apparatus as herein described dependents on various factors that are identifiable by those skilled in the art, including but not limited to the type and/or nature of the sample, types of impurity entities present in the sample, target molecule to be purified and/or amplified In some embodiments, the containment vessel (301, 501) is sealed when the sample collection element (302, 502) is removably coupled to the containment vessel.

In some embodiment, the apparatus further comprises a loading port (305), and the plurality of reagents (330) are configured for loading or extracting though the loading port for placement in or removal from fluid communication with the nucleic acid binding element (304).

In some embodiments, the sample collection element (302, 502) comprises a lumen (310, 510), and the sample collection element is configured to transfer the sample to the nucleic acid binding element (304, 504) via lavage delivered through the lumen when the sample collection element is removably coupled to the containment vessel (301, 501).

In some embodiments wherein the sample collection element (302, 502) comprises a lumen (310, 510), the plurality of reagents (330, 530) are configured for loading through the lumen for placement in fluid communication with the nucleic acid binding element (304, 504).

In some embodiments, the nucleic acid amplification reagents are suitable for isothermal amplification of the target nucleic acid. In particular, in some embodiments, the isothermal amplification is LAMP. In some embodiments, the isothermal amplification is HAD. In other embodiments, the isothermal amplification is RPA.

In some embodiments, the containment vessel (301, 501), the sample collection element (302, 502), the nucleic acid binding element (304, 504), the plurality of reagents (330, 530) and the heater (306, 506) are configured for a single use.

In some embodiments, the apparatus further comprises a waste collection unit (507) connected to the containment vessel (501). In particular, in some embodiments, the waste collection unit is coupled to the sample collection element (502), and comprises a chamber (601) and a plate (602). The chamber comprises a first gap (603). The plate is coupled to the chamber and comprises a second gap (604). The chamber and the plate surround the lumen (510) of the sample collection element, and at least one of the chamber and the plate is configured to be rotatable. When the first gap overlaps with the second gap, content of the containment vessel can flow into the chamber of the waste collection unit. The chamber and the plate can be made of silicon or coated with silicon.

The term "content" as used herein indicates any type of content comprised in the containment vessel including but not limited to one or more of the plurality of reagents, nucleic acid purification reagents, nucleic acid amplification reagents, samples, dyes, fluid or product generated during sample acquisition, preparation, nucleic acid purification, amplification and detection.

In some embodiments, the waste collection unit (507) is configured for collecting a waste, such as excessive reagents, dyes, fluid or product generated during and/or after sample acquisition and preparation, which includes nucleic acid amplification.

In some embodiments, the plurality of reagents (530) are comprised in the apparatus for selectively releasing of the reagents. For example, in some embodiments, the plurality of reagents are enveloped within a plurality of reagent cartridges (515). The plurality of reagent cartridges each comprises a capsule (516) and a plug (517), and the capsules are connected to the lumen (510) of the sample collection element (502) through an opening (518). The plug seals the opening. The plurality of reagent cartridges are configured to load the plurality of reagents through the lumen upon removal of the plug from the opening.

Figure 7:
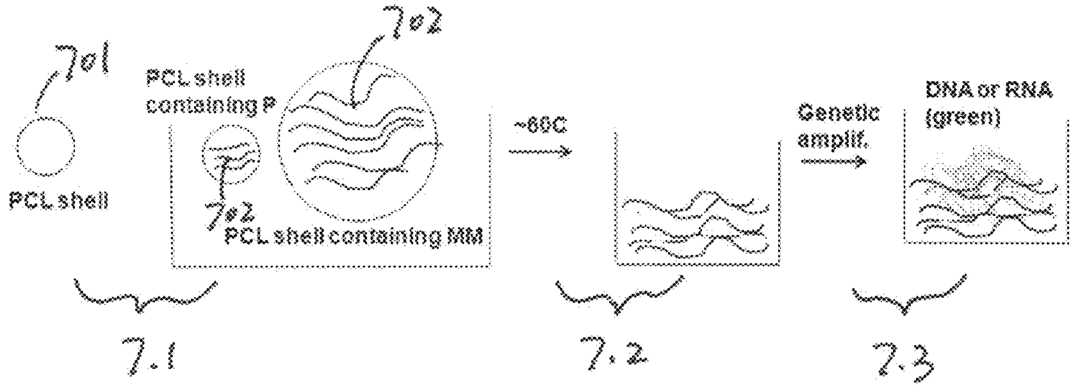
FIG. 7 shows sequestration of nucleic acid amplification master mix and enzyme in separate PCL shells and temperature-based release of the shell contents according to several embodiments.

In some embodiments, the nucleic acid amplification reagents (702) are sequestered in separate polymer cells (701), which are configured to melt and to release the nucleic acid amplification reagents when heated by the heater (see FIG. 7). Nucleic acid amplification reagents, for example, the polymerase and the master mix are isolated in separate polymer shells (Step 7.1), which are biocompatible and melt at 60° C. Upon heating to 60° C., the polymer shells melt to release the polymerase and master mix (Step 7.2), and nucleic acid amplification proceeds (Step 7.3). In some embodiments, the polymer shells are polycaprolactone (PCL) shells.

The term "sequestered" or "sequestration" as used herein refers to isolation of a component from a component containing environment to prevent mixing and/or reacting of the component with the environment and/or other components present in the environment.

In some embodiments, the sample collection element comprises a bodily sample collection element (303, 503). In particular, in some embodiments, the bodily sample collection element is suitable for collecting from the group consisting of nasal mucus, urine, fecal matter, blood, saliva, buccal cells and combination thereof. In some embodiments, the bodily sample collection element is a swab.

In some embodiments, the nucleic acid binding element (304, 504) is configured to lyse cells, denature proteins, bind nucleic acid and protect nucleic acid from damage or degradation. In particular, in some embodiments, the nucleic acid binding element comprises a FTA card. (see Example 2). In other embodiments, the nucleic acid binding element comprises a filter paper punch.

The term "FTA card" as used herein indicates a filter paper, such as produced by Whatman®, which contains chemicals that lyse cells, denature proteins and protect nucleic acids from nucleases, oxidative, and UV damage. Using FTA cards in conjunction with suitable nucleic acid purification reagents, such as the Whatman® Purification Reagent and a wash buffer can clean up complex tissue and/or impurity matrix in a sample, and separate out and retain genetic materials contained in the sample.

In some embodiments, the heater (306, 506) is configured to isothermally heat the nucleic acid binding element in fluid communication with the nucleic acid amplification reagents to a temperature in the range of 60° C.-65° C. for a duration of up to one hour.

In some embodiments, the heater (306) comprises a control unit (320) and a heating unit (350). The heating unit comprises a plurality of heating blocks (340) configured to house the containment vessel (301) and heat the nucleic acid binding element (304) position in the containment vessel.

In some embodiments, the heater (306) comprises an electrical power source. In particular, according to some embodiments, the heater comprises a fuel cell.

In other embodiments, the heater (606) can be a chemical heated heater. In particular, in some embodiments, the chemical heater may be used in conjunction with a phase change material, such as paraffin, to maintain a steady temperature during heating.

In particular, in some embodiments, the chemical heater is configured to generate heat through an exothermal chemical reaction identifiable by a skilled person. Examples of such chemical reactions include but are not limited to crystallization of a supersaturated salt solution, such as sodium acetate. A supersaturated solution of sodium acetate in water may be activated by bending a metal disc which starts a crystallization process. Once the reaction is activated, the sodium acetate crashes out of solution, resulting in an exothermic reaction that lasts about an hour, which is dependent upon temperature profile of environment, volume to be heated, etc. Another example of an exothermal chemical reaction is iron oxidation. The ingredients to the reaction are iron, water, cellulose, vermiculite, activated carbon and salt. The iron oxidizes upon exposure to oxygen, producing iron oxide and heat. The salt acts as a catalyst for the reaction. Carbon helps disperse the heat, and the vermiculite is used as an insulator for the purpose of retaining the heat. The cellulose is added as filler.

Accordingly, in some embodiments, the heater is configured to generate heat using a supersaturated salt solution. In other embodiments, the heater is configured to generate heat via metal oxidation. In other embodiments, the heater comprises a catalytic burner.

In some embodiments, the apparatus further comprises a detection unit (520) configured to detect amplification of the target nucleic acid. In particular, in some embodiments, the detection element comprises a colorimetric dye in fluid communication with the nucleic acid amplification reagents, which undergoes a color shift when the target nucleic acid is amplified. In other embodiments, the detection element comprises a fluorescent dye in fluid communication with the nucleic acid amplification reagents, which fluoresces when the target nucleic acid is amplified. The dyes can be introduced concurrently with the nucleic acid amplification reagents or separately into fluid communication with the nucleic acid amplification reagents after the amplification, for example, from one of the reagent cartridges (see Example 3, FIG. 10).

The dyes can be any colorimetric dyes or fluorescent dye identifiable by a skilled person. For example, in some embodiments, the colorimetric dye can be hydroxynaphthol blue (HNB). HNB denotes target amplification to the unaided eye via a color shift that stems from changes in the concentration of $Mg^{2+}$ in solution: free $Mg^{2+}$ in the reaction solution binds to pyrophosphate that is generated as deoxynucleotide triphosphates are added to growing amplification product, forming magnesium pyrophosphate. In other embodiments, the colorimetric dye can be picogreen, which is a fluorescent intercalating dye.

In other embodiments, the detection element comprises a lateral flow dipstick (LFD).

According to another aspect of the disclosure, apparatus for diagnosing a condition in an individual is described. The condition is associated to presence of a target nucleic acid in the individual, which is produced by certain pathogens.

The term "condition" as used herein indicates a physical status of the body of an individual (as a whole or as one or more of its parts), that does not conform to a standard physical status associated to a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "individual" as used herein in the context of diagnosing a condition includes a single biological organism, including but not limited to, animals and in particular higher animals and in particular vertebrates such as mammals and in particular human beings.

The term "pathogen" as used herein indicates a biological agent that may cause an infection or infectious disease in a host. The term "infection" as used herein indicates presence and/or colonization of an infecting species of pathogen in a host organism. During infection, the pathogen seeks to use the host's resources to survive and reproduce, often resulting in one or more infectious diseases. The term "infectious disease" as used herein indicates clinically evident illness that may have characteristic medical signs and/or symptoms, resulting from infection, presence and growth of an infecting species of pathogen in a host organism. In some cases, an infectious disease may be asymptomatic for much or all or their course, known as the latency period. A pathogen can be naturally occurring microbe or microorganism, including a virus, bacterium, prion, fungus or parasites or be produced by deliberate human agency.

In some embodiments, the pathogen can be, for example, viruses, bacteria, fungi, and combinations thereof.

In some embodiments, the condition is an infectious disease. In particular, in some embodiments, the infectious disease can be, for example, foot and mouth disease, flu, swine flu, avian flu, MRSA, anthrax, STDs, AIDS, CT/NG, HPV, HCV, C. Diff, Strep A, Influenza and combinations thereof.

Figure 4A:
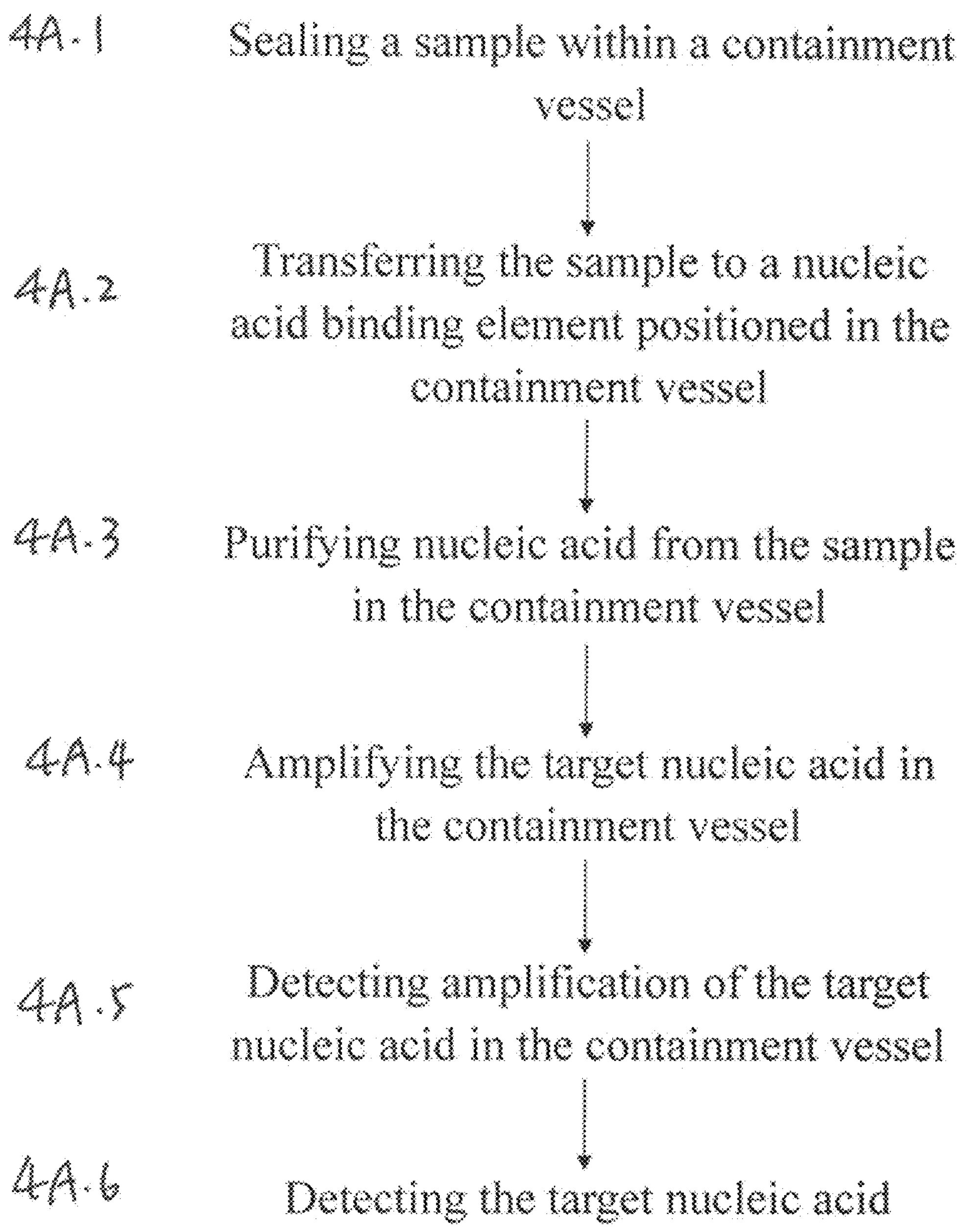
FIG. 4A shows a procedural flow chart of a method for detecting a target nucleic acid in a sample.

According to another aspect of the disclosure, methods for detecting a target nucleic acid in a sample are described. In some embodiments, the method comprises sealing the sample within a containment vessel, transferring the sample to a nucleic acid binding element position in the containment vessel, purifying nucleic acid from the sample in the containment vessel, amplifying the target nucleic acid in the containment vessel, detecting amplification of the target nucleic acid in the containment vessel, and detecting the target nucleic acid. FIG. 4A shows a procedural flow chart illustrating the steps 4A.1-4A.6 according to these embodiments.

In some embodiments, the method further comprises collecting the sample before the sealing. In particular, in some embodiments, collecting the sample further comprises collecting a bodily sample, such as conducting a nasal swab, collecting a blood sample, collecting a saliva sample, collecting a nasal mucus sample, collecting a urine sample, collecting a buccal cell sample, or collecting a fecal sample.

In some embodiments, collecting the sample further comprises collecting the sample with a sample collection element. In particular, in some embodiments, sealing the sample within a containment vessel comprises removably coupling the sample collection element to the containment vessel.

In some embodiments, the sample collection element comprises a lumen, and transferring the sample is performed by lavaging the sample through the lumen of the sample collection element when the sample collection element is removably coupled to the containment vessel.

In some embodiments, purifying and amplifying nucleic acid further comprises introducing a plurality of reagents suitable for nucleic acid purification and amplification into fluid communication with the nucleic acid binding element. In particular, in some embodiments, the introducing is performed through introducing the plurality of reagents from a plurality of reagent cartridges. In some embodiments, the plurality of reagent cartridges may be connected directly to the containment vessel.

Additionally, in those embodiments where the sample collection element comprises a lumen, the plurality of reagent cartridges may be coupled to the sample collection element and connected with the lumen. In these embodiments, the plurality of reagents can be delivered from the reagent cartridges through the lumen into the containment vessel for placement in fluid communication with the nucleic acid binding element located in the containment vessel.

In some embodiments, the purification further comprises collecting a waste into a waste collection unit which is connected to the containment vessel.

In some embodiments, the nucleic acid amplification reagents are sequestered within separate polymer shells. The polymer shells are comprised within the containment vessel and are configured to melt and release the nucleic acid amplification reagents into fluid communication with the nucleic acid binding element upon heating the polymer shells. In some embodiments, the polymer shells can be polycaprolactone (PCL) shells.

In some embodiments, amplifying the target nucleic acid further comprises heating the nucleic acid binding element in fluid communication with nucleic acid amplification reagents. In particular, in some embodiments, the heating further comprises isothermally heating the nucleic acid binding element in fluid communication with the nucleic acid amplification reagents to a temperature in the range of 60° C. to 65° C. for a duration of up to one hour.

In some embodiments, the heating is performed by using a disposable heater.

In some embodiments, the heating is performed by heating via an exothermic chemical reaction identifiable by a skilled person. For example, the heating can be performed by heating via an oxidative chemical reaction or a catalytic chemical reaction.

In some embodiments, detecting amplification of the target nucleic acid comprises detecting a color shift in a colorimetric dye or detecting fluorescence of a fluorescent dye. The dyes can be introduced concurrently with the nucleic acid amplification reagents or separately into fluid communication with the nucleic acid amplification reagents after the amplification, for example, from one of the reagent cartridges (see Example 3, FIG. 10). The colorimetric dye and the fluorescent dye can be the ones identifiable by a skilled person, including but not limited to hydroxynaphthol blue (HNB) and picogreen (see Example 2).

In other embodiments, detecting amplification of the target nucleic acid comprises detecting through a chromatography lateral flow dipstick (LFD).

In some embodiments, the method further comprises disposing the sample, the containment vessel, the sample collection element, nucleic acid binding element, the reagents and/or the heater after a single use.

According to another aspect of the current disclosure, a method for diagnosing a condition in an individual is described. The condition is associated to presence of a target nucleic acid in the individual, which is produced by certain pathogens. In some embodiments, the method comprises sealing a sample from the individual within a containment vessel, transferring the sample to a nucleic acid binding element position in the containment vessel, purifying nucleic acid from the sample in the containment vessel, amplifying the target nucleic acid in the containment vessel, detecting amplification of the target nucleic acid in the containment vessel, and diagnosing the condition. FIG. 4B shows a procedural flow chart illustrating the steps 4B.1-4B.5 according to these embodiments.

In some embodiments, the pathogen can be, for example, viruses, bacteria, fungi, and combinations thereof.

In some embodiments, the condition is an infectious disease. In particular, in some embodiments, the infectious condition can be, for example, foot and mouth disease, flu, swine flu, avian flu, MRSA, anthrax and combinations thereof.

Further details concerning the methods and apparatus can be identifiable by the person skilled in the art upon reading the present disclosure.

EXAMPLES

The methods and apparatus for detecting a target nucleic acid in a sample are further illustrated in the following examples, which are provided by way of illustration and are not intended to be limiting.

A person skilled in the art will appreciate the applicability and the necessary modifications to adapt the features described in detail in the present section, to additional methods, apparatus, type of sample and pathogens according to embodiments of the present disclosure.

Example 1

Methods and Materials

The following materials and methods were used in performing the experiments illustrated in the examples herein described.

Primers, Recombinant Template and Virus.

MRSA primers were designed using LAVA-LAMP software and were purchased from Biosearch Technologies.

MRSA primers are part of a publication in progress (Torres et al. BMC Bioinform submitted for publication). *S. aureus* strain FPR3757/USA300 genomic DNA (BAA-1556D-5, American Type Culture Collection Manassas, Va.), used as positiveMRSA template, was received as lyophilized powder and dissolved in 1×TE buffer (10 mMTris-HCl, pH 8.0, 1.0 mMEDTA, pH 8.0, sterile solution, (#T0226, Teknova, Inc., Hollister, Calif.) to an initial concentration of approximately 100 ng/μL. The exact DNA concentration was measured by the PicoGreen assay (P11496, Invitrogen Corp., Carlsbad, Calif.) on a Qubit fluorometer (Invitrogen Corp., Carlsbad, Calif.), and 1 ng/μL stock solutions were prepared and stored at −20° C. Our lowest level of detection, 0.05 pg, represents 17 copies of DNA.

The primers for pan-serotypic detection of FMDV and the performance of this assay (analytical sensitivity) have been previously published in Dukes et al., Arch. Virol., 2006, vol. 151, pp. 1093-1106, herein incorporated by reference in its entirety. Recombinant template was used for initial FMDV experiments. In order to produce recombinant template, a synthetic double-stranded DNA target sequence representing an ~200 nt portion of the 3D RNA polymerase gene was prepared by Genscript Corporation and inserted into the pUC57 and pGS-21a vectors. Approximately 4 μg of each were prepared. The pGS-21a vector allows for the preparation of single-stranded RNA template using T7 RNA polymerase. 100 μl recombinant RNA template was applied to prototype swabs at a $10^{-4}$ dilution in DEPC water (Ambion).

For live virus testing, an epithelial homogenate (10% suspension in PBS) was prepared under BSL3 (UK SAPO4 containment—Specified Animal Pathogens Order) conditions from tongue tissue collected from cattle experimentally infected with O1-Manisa strain FMDV. The performance of the LAMP assay system was evaluated using prototype swabs that were dipped in 100 μL of the suspension at $10^{-1}$, $10^{-2}$, and $10^{-5}$ dilutions. Presence of FMDV in this material was verified by automated real-time RT-PCR targeting the 3-D region of the FMDV genome (Reid et al., J. Vet. Diagn. Invest., 2009, vol. 21, pp. 321-330).

LAMP and RT-LAMP.

LAMP/RT-LAMP is a robust, isothermal nucleic acid amplification method. Master mix and enzymes were added to prototype tubes via the and heated to 63° C. for between 45 min and 1 h. Reactions included primer solutions prepared by combining 40 μL each of 100 μM FIP and 100 μM BIP, 5 μL each of 100 μM F3 and 100 μM B3, and 20 μL each of 100 μM LF and 100 μMLB, and 370 μl of TE buffer, resulting in 500 μL of combined primer solution. reaction volumes of 100 μL for MRSA assays comprised 25 μL of combined primer solution plus 70-μL base mix [1.4 mM each dNTPs (Roche Diagnostics, Basel, Switzerland), 0.8 M betaine (Sigma, St. Louis, Mo.), 4.1 mM MgSO4 (New England Biolabs, Ipswich, Mass.), 1× Thermopol buffer (New England Biolabs), and 100 μM hydroxynaphthol blue (HNB) (Dojindo Laboratories) in DEPC water (Ambion)] and 5 μL BST polymerase (New England Biolabs).

FMDv Master Mix was slightly modified and included 4 μL BST polymerase, as well as 0.3 μL Thermoscript RT (Invitrogen, Carlsbad, Calif.) per 100-μL reaction volume.

HNB indicates target amplification to the unaided eye via a color shift that stems from changes in the concentration of $Mg^{2+}$ in solution: free $Mg^{2+}$ in the reaction solution binds to pyrophosphate that is generated as deoxynucleotide triphosphates are added to growing amplification product, forming magnesium pyrophosphate (Goto et al., Biotechniques, 2009, vol. 46, pp. 167-172). This is in contrast to fluorescent dyes, which fluoresce upon intercalation into amplification products but need an excitation source and electronic detection system.

Example 2

Prototype Device and Assay

A Point-Of-Care prototype device and assay have been designed, which encompasse sample acquisition, sample preparation/nucleic acid extraction, LAMP/RT-LAMP amplification, and detection in a single tube. A rendering of the prototype device is shown in FIGS. 3A-3B. The device includes a sealable polypropylene tube with a loading port, a hollow polyester swab coupled to a tube cap, a 4 mm disc of cellulose FTA card (Whatmann®) positioned within the tube, and reagents including dye for conducting sample preparation such as nucleic acid purification and RT-LAMP. The swab facilitates sample acquisition from surfaces, oral or nasal cavities, or lesions.

Figure 4C:
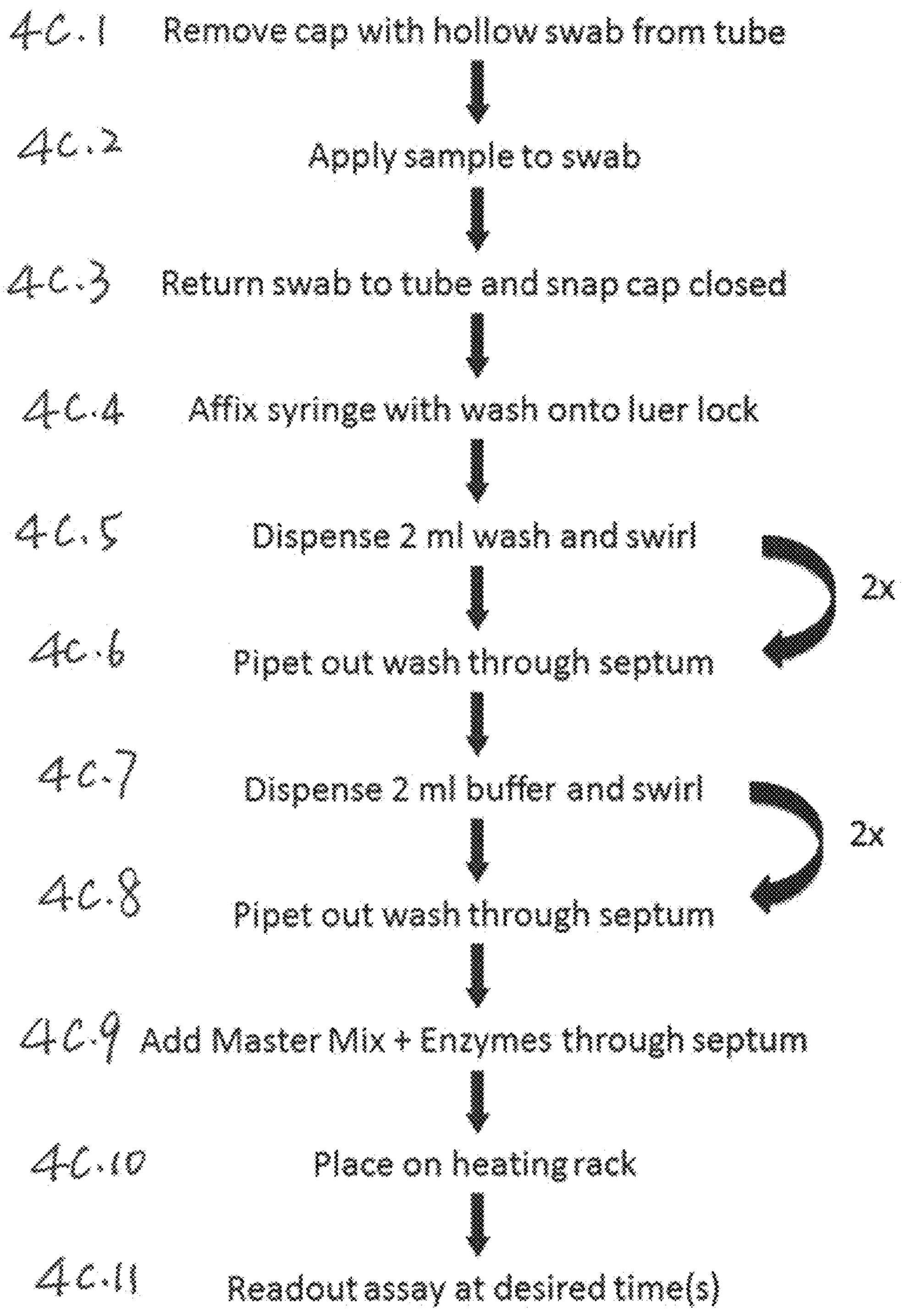
FIG. 4C shows a procedural flow chart of a method for integrated sample acquisition, preparation, nucleic acid extraction, amplification and detection all in one tube using the apparatus according to the present disclosure.

A procedural flow chat of performing the assay using the Point-Of-Care device is shown FIG. 4C. First, the cap with hollow swab is removed from the tube (Step 4C.1). Then, a Sample is collected by wiping material of interest with the hollow swab (Step 4C.2). After sample collection, the swab is returned to the tube, and the tube cap is secured in a manner that precludes re-opening of the tube (step 4C.3). A first syringe containing 4 ml of Purification Reagent (Whatman®) is attached to a luer lock (308) fitting on the cap (307) (Step 4C.4), and then 2 ml of the Purification Reagent is delivered through the swab lumen to immerse the sample in a purification wash (Step 4C.5). The tube is swirled and set in a rack for approximately 2 min, followed by waste removal through the tube's lower loading port (for example, a septum) (305) via a pipette (Step 4C.6). Purification Reagent steps then are repeated.

The first syringe is decoupled from the luer lock, a second syringe containing 4 ml TE buffer is attached, and 2 ml TE buffer is delivered through the swab lumen to rinse the sample (Step 4B.7). After swirling of the tube and about 2 min of waiting, waste is removed (Step 4B.8), and the TE buffer steps are repeated. At this point, sample has been transferred from the swab to the FTA disc and cleaned.

Next, LAMP/reverse transcriptase (RT-LAMP) master mix plus enzymes are pipetted into the evacuated tube through the loading port (Step 4C.9). One or more such assay tubes then are placed on the custom thermal heater rack (FIG. 3B), which is maintained at an isothermal temperature of about 63° C. for 45 min to 1 hr., to conduct RT-LAMP amplification (Step 4C.10). Positive amplification is determined by a visible color change in the reagents from purple to blue, due to the presence of colorimetric dye (Step 4C.11).

Example 3

Detection Under BSL3 Condition for Serotype O Foot and Mouth Disease Virus (FMDv)

Figure 2:
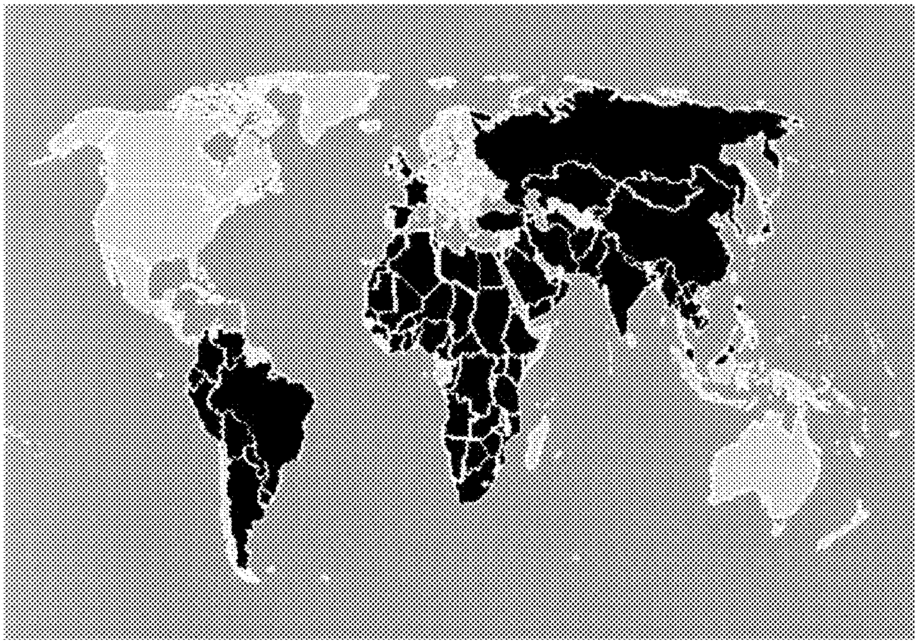
FIG. 2 shows Foot-and-mouth disease (FMD) is endemic in many parts of the world. In this map, black indicates countries where FMDv outbreaks have been reported between 1997-2008. Over the past few years, developing countries, including Sub-Saharan Africa, northern South America, Southeast Asia and the Middle East, have reported the most cases of FMD. (Data from U.N. Food and Agriculture Organization; U.N. Food and Agriculture Organization.)

Proof-of-concept validation of the Point-of-care methods and apparatus according to the current disclosure has been conducted by amplifying and detecting serotype O Foot-and-Mouth Disease virus (FMDv). Foot-and-Mouth Disease is a highly infectious viral disease of cloven-hoofed animals, including cows, sheep, goats and pigs. It is one of the most infectious diseases that affect livestock, and outbreaks can spread quickly. The virus can survive in contaminated fodder and the environment for up to one month and can survive in the lymph nodes and bone marrow of infected animals. There are at least seven different types and many subtypes of the FMD virus, the most common of which is serotype O (see FIG. 2).

Humans can spread FMDv through contaminated clothing, footwear, farm equipment and trucks. It also can spread through the air from one animal to another. Most commonly, it spreads through a contaminated source of water, hay or feed. FMDv epidemics have resulted in the slaughter of millions of animals, despite the fact that, frequently, it is non-fatal. Culling is primarily performed to halt disease spread, as growth and milk production may be permanently affected in recovered animals. Infection also may lead to trade bans on affected countries.

The UK FMD epizootic in September of 2001 led to a $17 billion cost to the economy. 2,030 farms were infected; 15,000 antigen tests, and more than 1 million ELISA tests, were performed. Average time from field collection to receipt at a centralized laboratory was 1.2 days, so many decisions were based on clinical diagnosis without laboratory confirmation. No evidence was found in 23% of all farms declared infected.

Clearly, FMDv has substantial relevance to veterinary medicine and represents a virus with enormous economic impact that would benefit from in-the-field POCT in accordance with the prototype device (Ferris et al., 2006, Vet. Rec., Vol. 159, pp 373-378).

Figure 8:
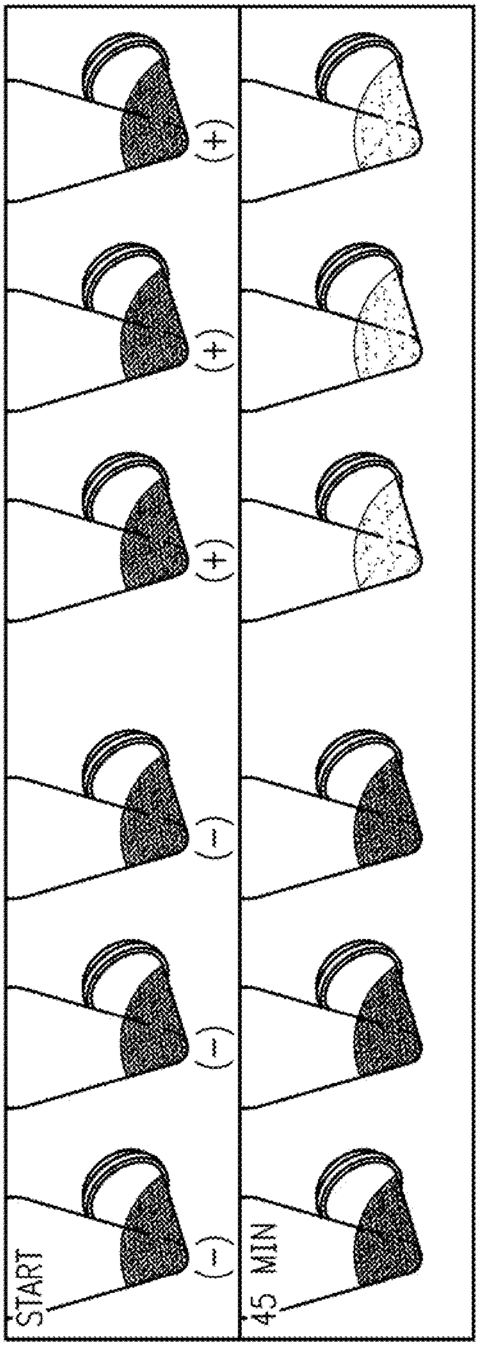
FIG. 8 shows images showing colorimetric detection of recombinant FMDv template: 3 negative, no template controls (−) and 3 positive template (+) samples are shown. (−) tubes remain violet while (+) tubes shift to blue.
Figure 9:
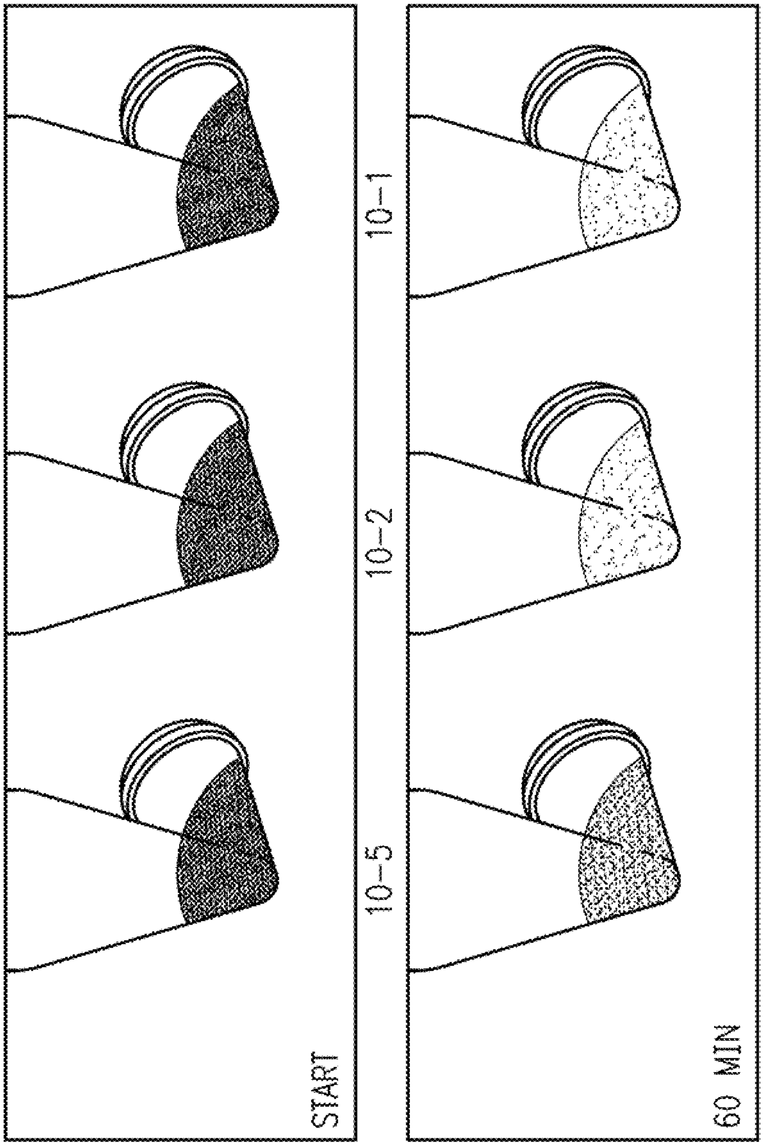
FIG. 9 shows images of live FMDv dilution series from tissue homogenate run in prototype containment tubes. Top panel indicates starting reaction colors, and lower panel indicates reaction mix colors at 60 min. While material in all tubes amplified, reaction mixture colorimetric results show a violet purple to blue transition with increasing virus concentration.
Figure 11A:
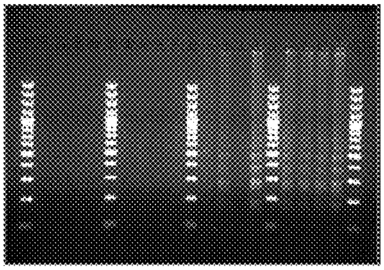
FIGS. 11A-B show time sequence gel electrophoresis results from samples run in prototype reaction tubes.
Figure 11B:
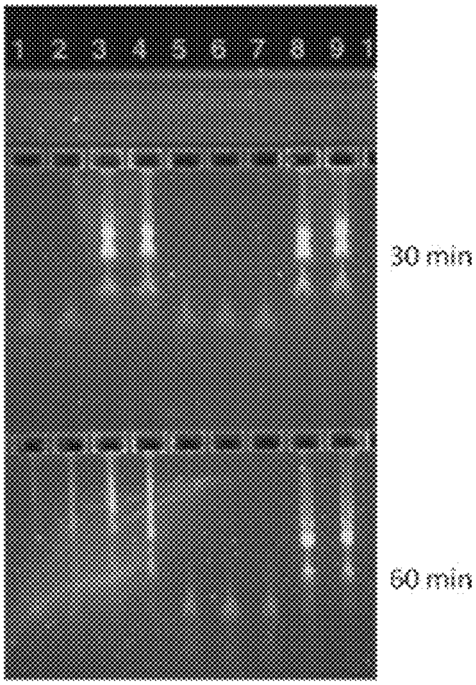

Point-of-care testing on recombinant FMDv, and clinical isolate tissue homogenate (live virus, BSL3, Pirbright, UK) was performed. FIG. 8 shows exemplary images of negative, no template controls (NTC) and positive, template controls run with recombinant template at the start and at 45 min. Electrophoresis gels were run on 2 μL aliquots removed from the loading port to confirm colorimetric results (FIG. 11A). FIG. 9 shows images of a dilution series of live FMDV taken at start and 60 min. A gel was run to confirm the colorimetric results (FIG. 11B). The results indicate that, while performing the entire FMDV assay in a single disposable tube, we can colorimetrically detect virus diluted down to $10^{-5}$ dilution in about 45 min. Parallel testing of these samples (in triplicate) by real-time RT-PCR generated $C_T$ values (±standard deviation) of 15.7±0.1, 19.6±0.3, and 31.0±0.1 for the $10^{-1}$, $10^{-2}$, and $10^{-5}$ dilutions, respectively.

Figure 10:
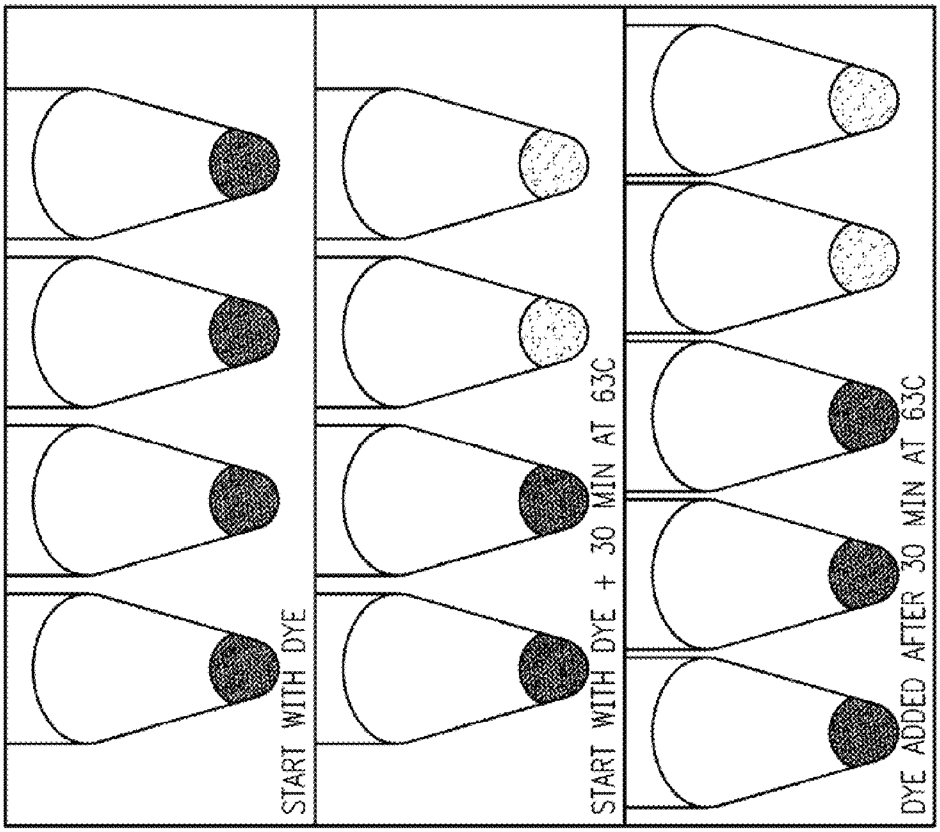
FIG. 10 shows colorimetric detection of recombinant FMDv after 30 min.

FIG. 10 shows colorimetric detection of recombinant FMDv after 30 min. Top panel indicates initial color of HNB dye in 25 mL reactions covered with a drop of mineral oil. Middle panel shows a shift from purple to blue by 30 min in tubes 3 and 4, which contained 5 mL template material (tubes 1 and 2 were no template controls). Lower panel compares colorimetric detection upon adding dye at 30 min timepoint, as opposed to incorporating it at reaction initiation (first 3 tubes no template; tubes 4 and 5 contained 5 mL template).

Example 4

Detection Under BSL1 Condition for MRSA Genomic DNA

Figure 12:
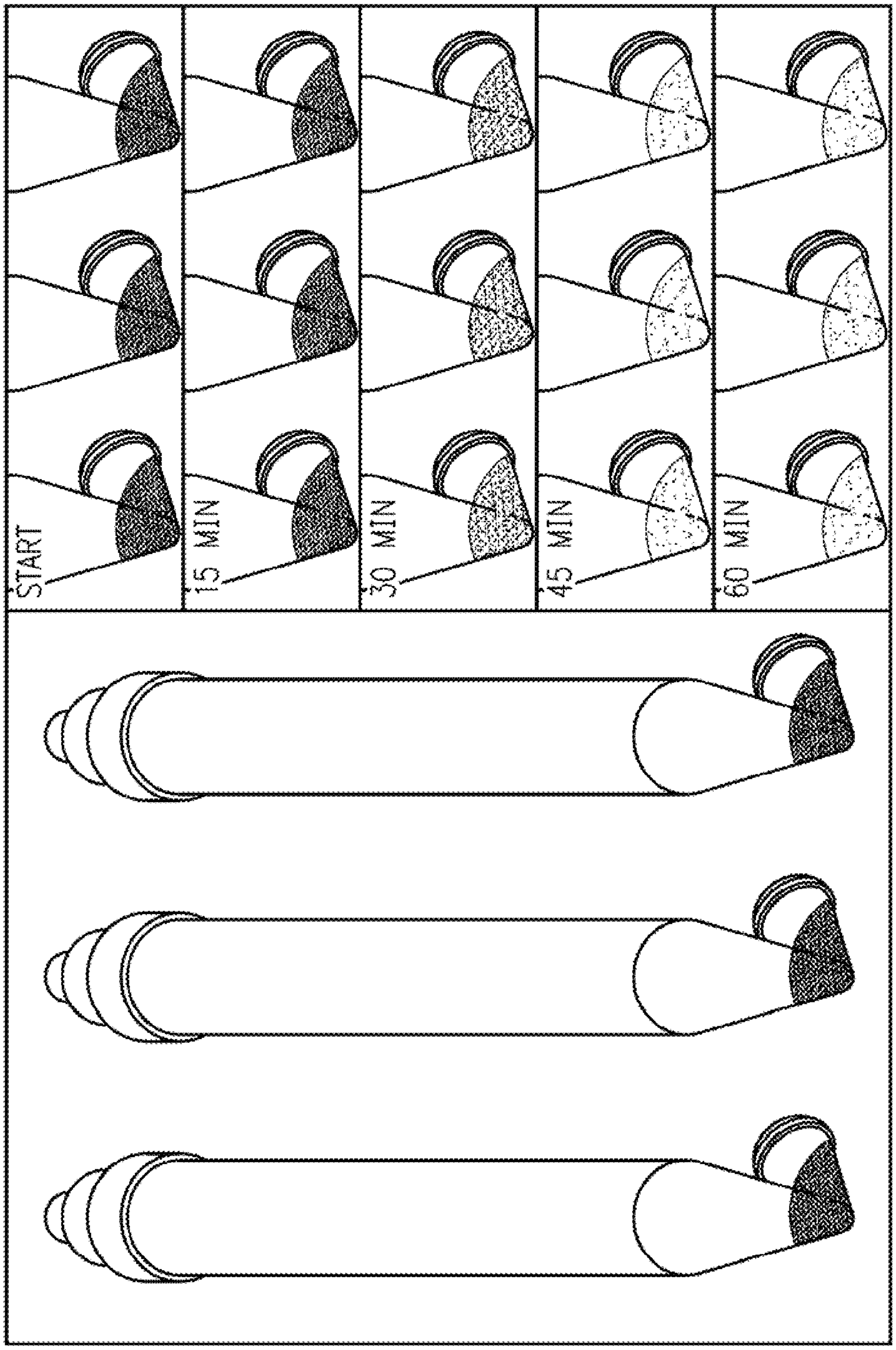
FIG. 12 shows time series images of initial MRSA assay in device tubes according to several embodiments. The swabs were dipped in 100 μL of 10 pg/μL DNA.
Figure 13:
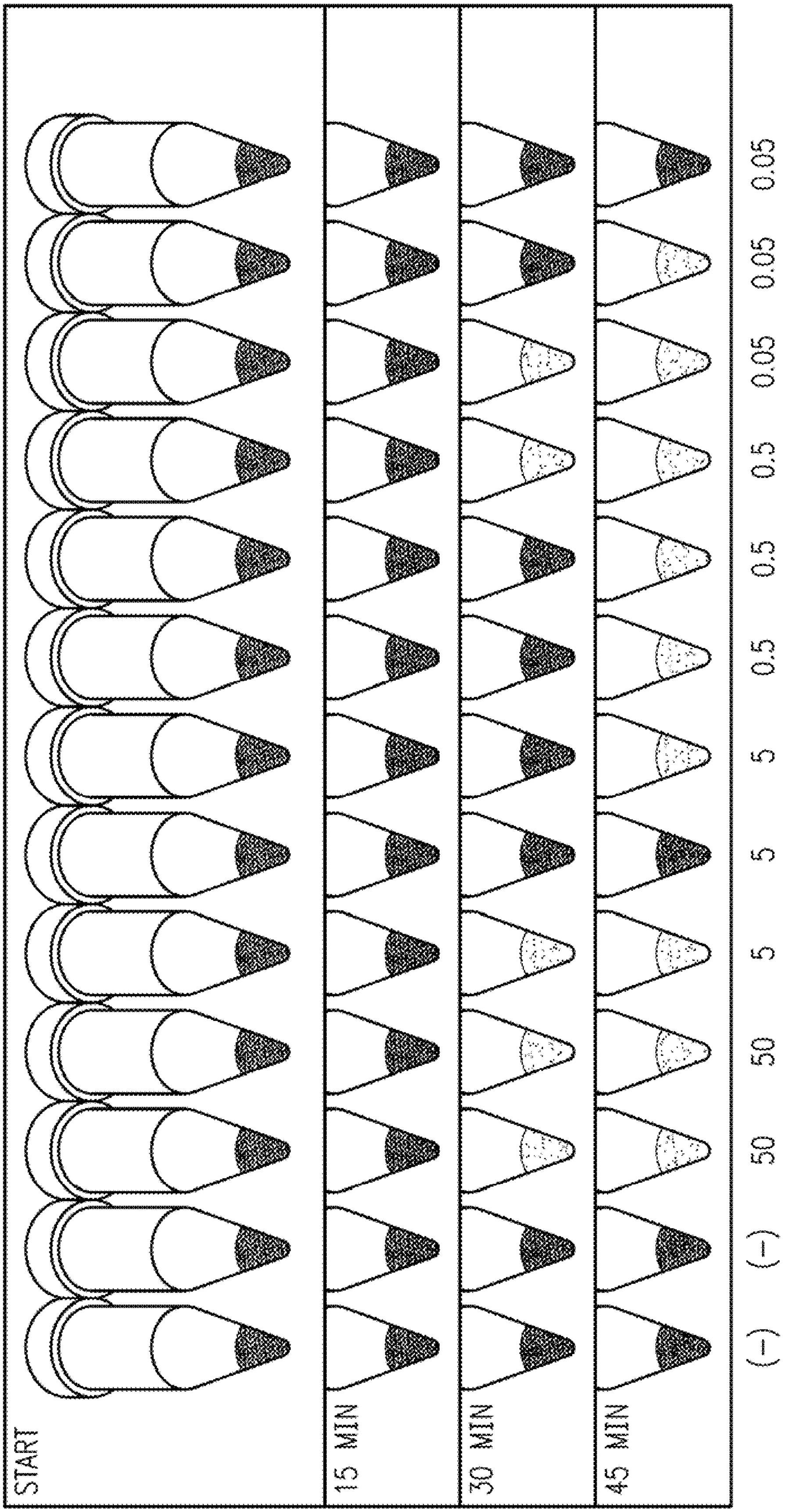
FIG. 13 shows time series images of MRSA assay in microcentrifuge tubes. (−) represents no template controls. Numbers indicate pg DNA per reaction. Most dilute MRSA genomic DNA samples on right contain ~17 copies of DNA.

FIG. 12 shows time series images of MRSA assay in prototype tubes. Genomic DNA transferred from swabs to filter paper during sample preparation and amplification was performed on material embedded in the paper. FIG. 13 shows a 45-min MRSA assay in microcentrifuge tubes in order to assess preliminary assay sensitivity. Data indicate that the colorimetric assay can detect ~17 genomic copies of MRSA. Water served as no template control (NTC). Four percent agarose gels corroborated sequence amplification in solutions that turned blue, and lack of amplification in solutions that remained purple.

The examples set forth above and in the enclosed appendixes herein incorporated by reference in their entirety, are provided to give those of ordinary skill in the art a complete disclosure and description of how to make and use the embodiments of the devices, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the disclosure (including appendices) are indicative of the levels of skill of those skilled in the art to which the disclosure pertains. All references cited in this disclosure (including appendices) are incorporated by reference to the same extent as if each reference had been incorporated by reference in its entirety individually.

The entire disclosure of each document cited (including patents, patent applications, journal articles, abstracts, laboratory manuals, books, or other disclosures) is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

LIST OF REFERENCES

1. McClure et al. BMC Res. Notes, "*Assessment of DNA extracted from FTA cards for use on the Illumina iSelect BeadChip*" 2009, vol. 2, pp. 107-110.
2. Beckett et al., Am. J. Epidemiol., "*Buccal swabs and treated cards: Methodological considerations for molecular epidemiologic studies examining pediatric populations*" 2008, vol. 167, pp. 1260-1267
3. Dukes et al., Arch. Virol., "*Novel reverse transcription loop-mediated isothermal amplification for rapid detection of foot-and mouth disease virus*" 2006, vol. 151, pp. 1093-1106.
4. Reid et al., J. Vet. Diagn. Invest., "*Performance of real-time RT-PCR for the detection of foot-and-mouth disease virus during field outbreaks in the United Kingdom in* 2007", 2009, vol. 21, pp. 321-330.
5. Goto et al., Biotechniques, "*Colorimetric detection of loop-mediated isothermal amplification reaction by using hydroxynaphthol blue*", 2009, vol. 46, pp. 167-172.
6. Notomi. et al., Nucleic Acids Research, "Loop-mediated isothermal amplification of DNA", 2000, Vol. 28, e63
7. Vincent et al. EMBO reports, "*Helicase-dependent isothermal DNA amplification*", 2004, Vol. 5, pp. 795-800.
8. Mary Hoff, PLoS Biology, "*DNA Amplification and Detection Made Simple* (*Relatively*)" 2006, Vol. 2, e222.
9. Ferris et al., Vet. Rec., "*Comparisons of original laboratory results and retrospective analysis by real-time reverse transcriptase-PCR of virological samples collected from confirmed cases of foot-and-mouth disease in the UK in* 2001", 2006, Vol. 159, pp 373-378.

What is claimed is:

1. A method for detecting a target nucleic acid in a sample, the method comprising:

sealing the sample within a containment vessel, wherein the containment vessel has a container body defining a single unpartitioned cavity capable of holding the sample;

in the single unpartitioned cavity where the sample is sealed:

transferring the sample to a nucleic acid binding element positioned in the containment vessel;

introducing nucleic acid amplification reagents in fluid communication with the nucleic acid binding element;

isothermally heating the nucleic acid amplification reagents;

amplifying the target nucleic acid; and detecting amplification of the target nucleic acid.

2. The method of claim 1, further comprising collecting the sample before the sealing.

3. The method of claim 2, wherein collecting the sample comprises collecting a bodily sample from the individual.

4. The method of claim 3, wherein collecting a bodily sample further comprises conducting a nasal swab, collecting a blood sample, collecting a saliva sample, collecting a nasal mucus sample, collecting a urine sample, collecting a buccal cell sample, or collecting a fecal sample.

5. The method of claim 2, wherein collecting the sample further comprises collecting the sample with a sample collection element.

6. The method of claim 5, wherein the sealing further comprises reversibly fastening the sample collection element to the containment vessel.

7. The method of claim 6, wherein the sample collecting element comprises a lumen, and wherein the method further comprises transferring one or more reagent through the lumen of the sample collection element when the sample collection element is reversibly fastened to the containment vessel.

8. The method of claim 1, further comprising purifying nucleic acid from the sample in the cavity after the transferring.

9. The method of claim 8, wherein the purifying comprises introducing nucleic acid purification reagents into fluid communication with the nucleic acid binding element.

10. The method of claim 9, wherein the introducing further comprises introducing the nucleic acid purification reagents from a plurality of reagent cartridges into fluid communication with the nucleic acid binding element, wherein the plurality of reagent cartridges are connected to the containment vessel.

11. The method of claim 9, wherein the purifying further comprises collecting a waste into a waste collection unit connected to the containment vessel.

12. The method of claim 1, wherein the introducing further comprises introducing the nucleic acid amplification reagents from a plurality of reagent cartridges into fluid communication with the nucleic acid binding element, wherein the plurality of reagent cartridges are connected to the containment vessel.

13. The method of claim 1, wherein the nucleic acid amplification reagents are sequestered within separate polymer shells, the polymer shells comprised within the cavity and configured to melt and release the nucleic acid amplification reagents upon heating, and wherein the introducing further comprises heating the polymer shells.

14. The method of claim 13, wherein the polymer shells are polycaprolactone (PCL) shells.

15. The method of claim 1, wherein the heating further comprises isothermally heating the nucleic acid amplification reagents in fluid communication with the nucleic acid binding element to a temperature in the range of 60° C. to 65° C. for a duration of up to one hour.

16. The method of claim 1, wherein the heating further comprises heating via an exothermic chemical reaction.

17. The method of claim 1, wherein the heating further comprises heating via an oxidative chemical reaction.

18. The method of claim 16, wherein the heating further comprises stabilizing a heating temperature using a phase change material.

19. The method of claim 17, wherein the heating amplifying further comprises stabilizing a heating temperature using a phase change material.

20. The method of claim 1, wherein the heating further comprises heating via a catalytic chemical reaction.

21. The method of claim 1, wherein the heating further comprises heating via a disposable heater.

22. The method of claim 1, wherein detecting amplification of the target nucleic acid further comprises detecting a color shift in a colorimetric dye in fluid communication with the nucleic acid amplification reagents.

23. The method of claim 1, wherein detecting amplification of the target nucleic acid further comprises detecting fluorescence of a fluorescent dye in fluid communication with the nucleic acid amplification reagents.

24. The method of claim 1, further comprising disposing the sample, the containment vessel, the nucleic acid binding element and the nucleic acid amplification reagents after the detecting.

25. A method for diagnosing a condition in an individual, the condition being associated with presence of a target nucleic acid in the individual, the target nucleic acid being produced by a pathogen, the method comprising:

sealing a sample from the individual within a containment vessel, wherein the containment vessel has a container body defining a single unpartitioned cavity capable of holding the sample;

in the single unpartitioned cavity where the sample is sealed:

transferring the sample to a nucleic acid binding element positioned;

purifying nucleic acid from the sample;

introducing nucleic acid amplification reagents in fluid communication with the nucleic acid binding element;

isothermally heating the nucleic acid amplification reagents;

amplifying the target nucleic acid;

detecting amplification of the target nucleic acid; and diagnosing the condition.

26. The method of claim 25, wherein the pathogen is selected from the group consisting of viruses, bacteria, fungi, and combinations thereof.

27. The method of claim 25, wherein the condition is an infectious disease.

28. The method of claim 27, wherein the infectious disease is selected from the group consisting of foot and mouth disease, flu, swine flu, avian flu, MRSA, anthrax STDs, AIDS, CT/NG, HPV, HCV, C. Diff, Strep A, Influenza and combinations thereof.

29. A method for detecting a target nucleic acid in a sample, the method comprising:

collecting a sample with a sample collection element comprising a lumen;

sealing the sample within a containment vessel by reversibly fastening the sample collection element to the containment vessel, wherein the containment vessel has a container body defining a single unpartitioned cavity capable of holding the sample;

transferring the sample to a nucleic acid binding element positioned in the cavity by lavaging one or more reagents through the lumen of the sample collection element to the cavity when the sample collection element is reversibly fastened to the containment vessel;

introducing in the cavity nucleic acid amplification reagents in fluid communication with the nucleic acid binding element;

amplifying the target nucleic acid in the cavity by isothermally heating the nucleic acid amplification reagents; and detecting amplification of the target nucleic acid in the cavity.

30. The method of claim 1, wherein the single, unpartitioned container body has a cylindrical shape.

31. The method of claim 1, wherein the sample and nucleic acid amplification reagents are confined in the single unpartitioned cavity.

32. The method of claim 1, wherein the containment vessel is devoid of valves.

33. The method of claim 1 further comprising removing reagents from fluid communication with the nucleic acid binding element.

* * * * *